US012788378B2

(12) United States Patent
Marty

(10) Patent No.: US 12,788,378 B2
(45) Date of Patent: Nov. 10, 2026

(54) DEVICE FOR TAKING SAMPLES OF BONE MATTER

(71) Applicant: L'ETAT FRANçAIS REPRÉSENTÉ PAR LE MINISTÈRE DE L'INTÉRIEUR, Issy-les-Moulineaux (FR)

(72) Inventor: Julien Marty, Cergy-Pontoise Cedex (FR)

(73) Assignee: 'ETAT FRANçAIS REPRÉSENTÉ PAR LE MINISTÈRE DE L'INTÉRIEUR, Issy-les-Moulineaux (FR)

(*) Notice: Subject to any disclaimer, the term of this patent is extended or adjusted under 35 U.S.C. 154(b) by 200 days.

(21) Appl. No.: 18/551,343

(22) PCT Filed: Apr. 1, 2022

(86) PCT No.: PCT/FR2022/050621
§ 371 (c)(1),
(2) Date: Sep. 19, 2023

(87) PCT Pub. No.: WO2022/208036
PCT Pub. Date: Oct. 6, 2022

(65) Prior Publication Data

US 2024/0164760 A1 May 23, 2024

(30) Foreign Application Priority Data

Apr. 2, 2021 (FR) ...................................... 2103443

(51) Int. Cl.
*A61B 10/02* (2006.01)
*A61B 17/16* (2006.01)

(52) U.S. Cl.
CPC ........ *A61B 10/025* (2013.01); *A61B 17/1637* (2013.01); *A61B 2010/0208* (2013.01)

(58) Field of Classification Search
CPC .............. A61B 17/1635; A61B 10/025; A61B 17/32053; A61B 17/1637;
(Continued)

(56) References Cited

U.S. PATENT DOCUMENTS 4,055,362 A * 10/1977 Becker, III ............ B62B 5/0006
293/121
5,556,399 A 9/1996 Huebner
(Continued)

FOREIGN PATENT DOCUMENTS

FR 2625429 A1 7/1989

OTHER PUBLICATIONS

International Search Report and Written Opinion for International Application No. PCT/FR2022/050621, dated May 27, 2022.

*Primary Examiner* — Zade Coley
(74) *Attorney, Agent, or Firm* — LEASON ELLIS LLP

(57) ABSTRACT

The invention relates to a device (1) for taking samples of bone matter, comprising:

a support part (2) positioned at the proximal end (3) of the device (1), the support part (2) being equipped with a means (10) for coupling to a rotary tool, so as to rotationally drive the device (1);

a trephine (4) mounted removably on the support part (2), the trephine (4) being equipped at its distal end (5) with a cutting head (16) intended to come into contact with the bone matter; the trephine (4) and the support part (2) being hollow and together defining an internal housing within the device (1); the cutting head (16) comprising at its free end an opening (18) opening to the outside of the device (1), the opening (18) being in fluidic connection with the internal housing; and a removable collecting tube, positioned within the internal housing of the device (1) and open at one of its ends substantially facing the opening (18) of the cutting head (Continued)

(16), the collecting tube being intended to collect the bone matter cut by the trephine (4).
Application to the identification of human remains, notably in disasters, particularly air disasters.

13 Claims, 3 Drawing Sheets

(58) Field of Classification Search
CPC .. A61B 2017/00398; A61B 2010/0208; A61B 17/3472
See application file for complete search history.

(56) References Cited

U.S. PATENT DOCUMENTS

| | | | | | |
|---|---|---|---|---|---|
| 5,591,187 | A * | 1/1997 | Dekel | A61B 17/32002 | 606/180 |
| 5,632,747 | A * | 5/1997 | Scarborough | A61F 2/4644 | 606/86 R |
| 5,921,987 | A * | 7/1999 | Stone | A61F 2/30756 | 606/80 |
| 6,071,284 | A * | 6/2000 | Fox | A61B 17/1635 | 606/80 |
| 6,325,806 | B1 * | 12/2001 | Fox | A61B 10/0233 | 606/80 |
| 6,857,520 | B2 * | 2/2005 | Salazar | A61B 50/30 | 206/363 |
| 6,942,669 | B2 * | 9/2005 | Kurc | A61B 17/1635 | 606/80 |
| 2002/0058945 | A1 | 5/2002 | Steiner | | |
| 2002/0099382 | A1 * | 7/2002 | Salazar | A61B 50/30 | 606/86 R |
| 2004/0030343 | A1 * | 2/2004 | Kurc | A61B 17/1635 | 606/80 |
| 2004/0191897 | A1 * | 9/2004 | Muschler | A61B 17/32002 | 435/325 |
| 2007/0123909 | A1 * | 5/2007 | Rupp | A61B 17/92 | 606/104 |
| 2008/0234715 | A1 | 9/2008 | Pesce | | |
| 2009/0157082 | A1 * | 6/2009 | Meredith | A61F 2/46 | 606/84 |
| 2019/0159790 | A1 * | 5/2019 | Suriyan | A61B 17/176 | |
| 2020/0121328 | A1 * | 4/2020 | Lee | A61B 17/1637 | |

* cited by examiner

[Fig 1]
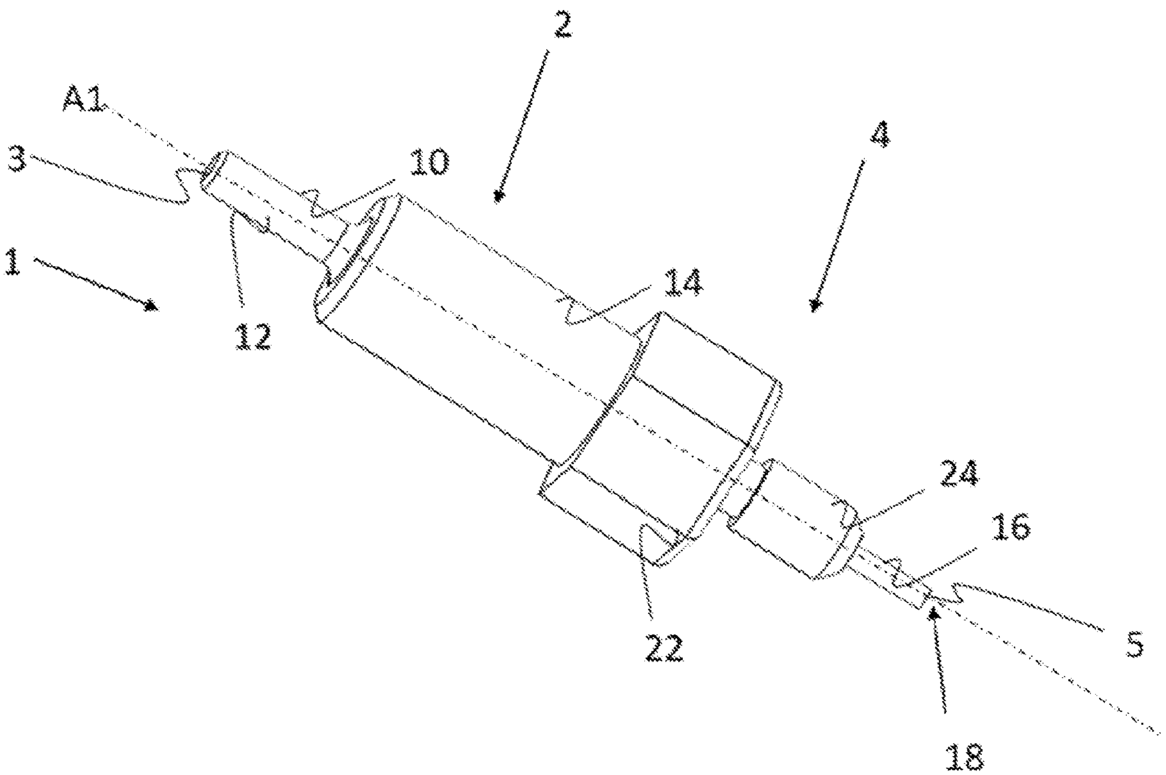
[Fig 2]
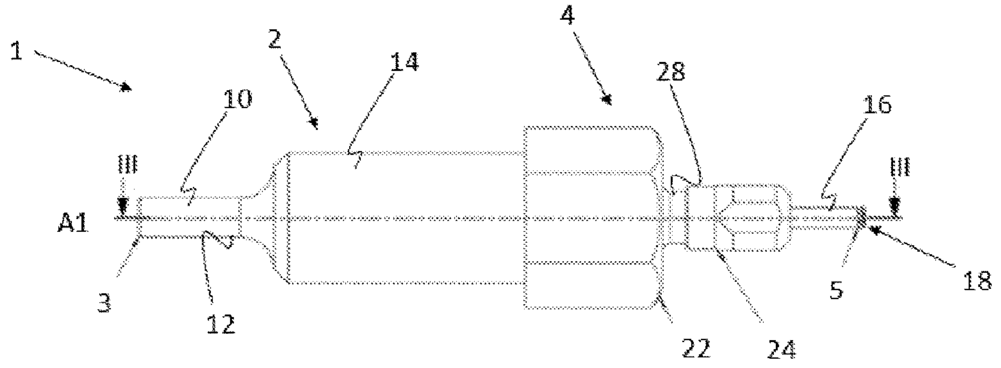

[Fig 3]
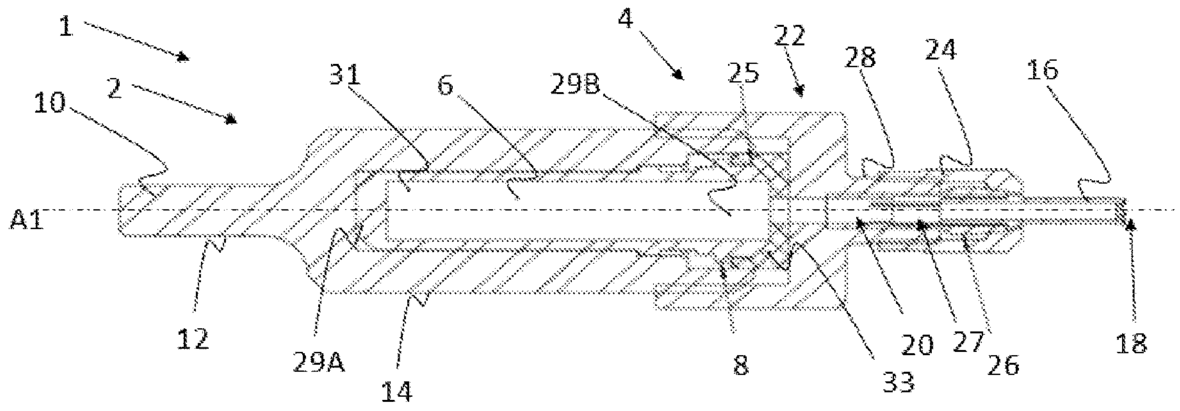
[Fig 4]
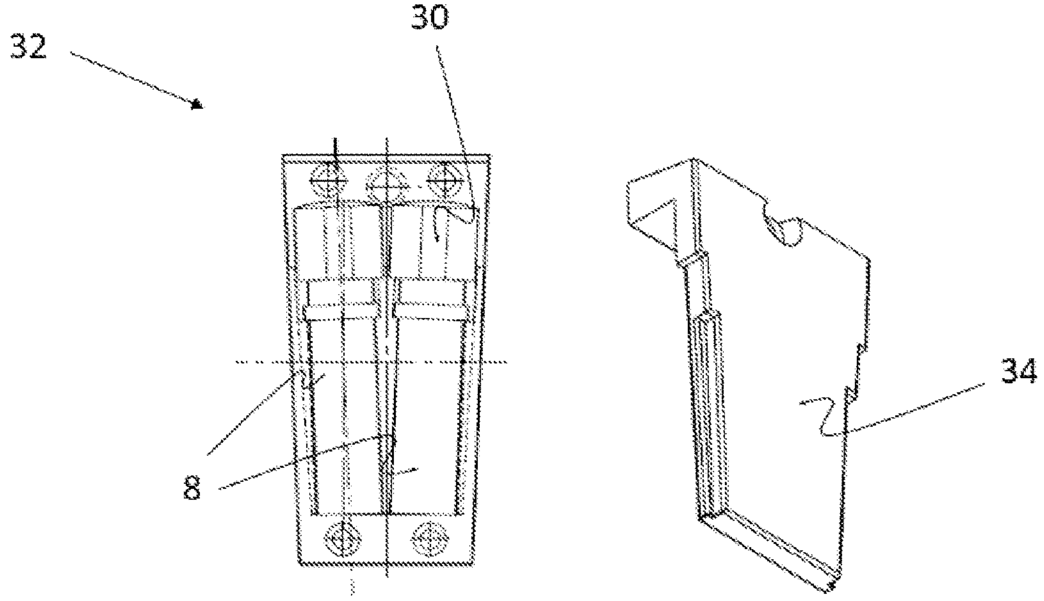

[Fig 5]
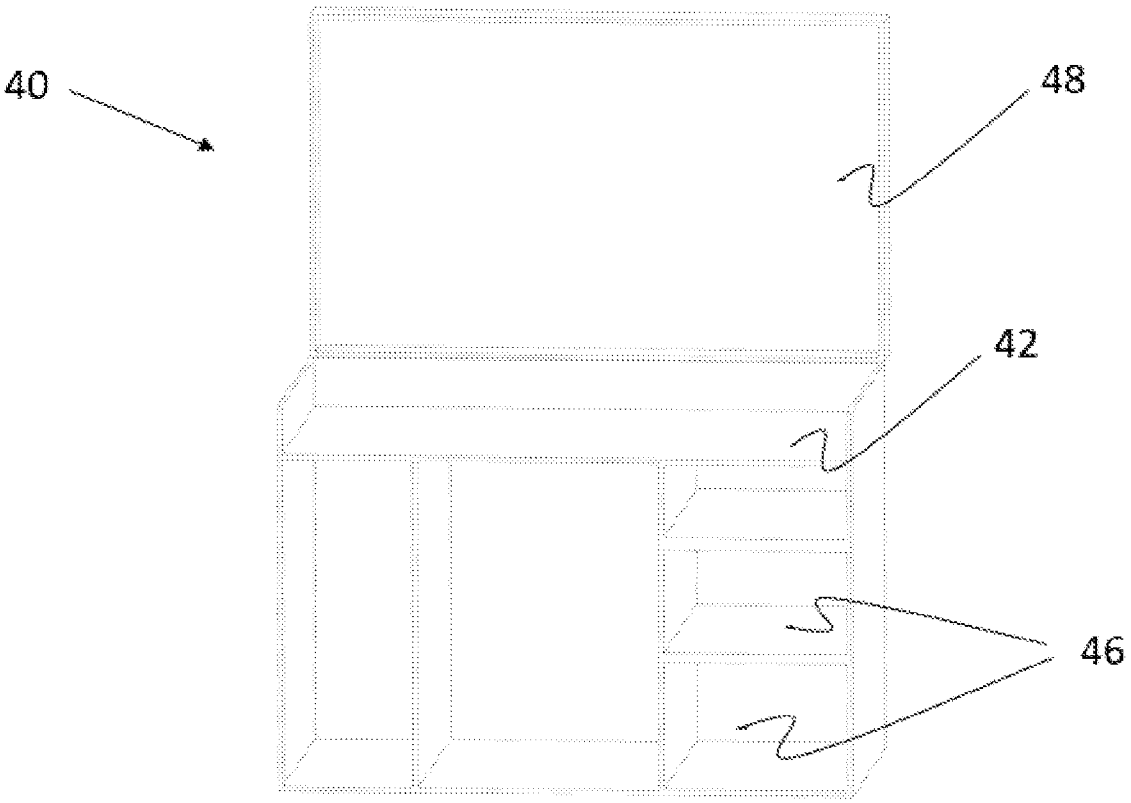

DEVICE FOR TAKING SAMPLES OF BONE MATTER

CROSS-REFERENCE TO RELATED PATENT APPLICATIONS

This application is a U.S. National Stage Application under 35 U.S.C. § 371 of International Patent Application No. PCT/FR2022/050621 filed Apr. 1, 2022, and French Patent Application No. 2103443 filed Apr. 2, 2021, both of which are incorporated by reference in their entireties. The International Application was published on Oct. 6, 2022, as International Publication No. WO/2022/208036 A1.

The present invention relates to a device for taking samples of bone matter intended to be mounted on a rotary tool of the portable power tool, an orthopedic drill, or a dental motor (or any other type of rotary tool). Such a sampling device is intended in particular for genetic analysis. In particular, this device can be used in the field of safety, for example in the context of criminal or forensic investigations for genetic analyses or genetic fingerprinting. The device is also suitable for any domain in which samples of small size are taken to be taken while minimizing the destruction of the object (for example, for the purposes of counter analysis, or preservation for museums).

Analysis of the DNA contained in bone fragments or teeth is a long and complex process. The first essential step of this process consists in taking a part of the bone matrix. This step is called sampling. At the end of sampling, the collected bone matrix is most often reduced to powder by mechanical grinding. A step of extracting DNA from this powder then follows. This extraction step makes it possible to lyse the cells constituting the bone matrix in order to release the DNA therefrom and then to purify this DNA from the other components of the cell lysate. In the context of human identification by genetic fingerprinting, the DNA thus purified is amplified by the PCR technique in order to simultaneously target and amplify a plurality of regions on the DNA having a polymorphism between the individuals. The amplification products thus obtained are finally identified by sequencing techniques known to the person skilled in the art.

Currently, sampling techniques from bone fragments for genetic fingerprinting described in the literature do not allow mobility, standardization, simplicity, speed and high-speed processing in a secure manner. Indeed, for this purpose most laboratories either use a hammer and an anvil, or perform a circular cut using oscillating or rotating saws commonly used in forensic science during autopsies.

The first solution, which consists in breaking the bones between two steel masses, is bulky and can generate a non-negligible projection of splinters, to say nothing of the presence in the laboratory of an anvil that is difficult to decontaminate and transport. During this operation, the operator cannot control the size of the debris obtained and must therefore strike the sample multiple times and then recover the fragments that they deem to be the correct size for the rest of the analyses.

The laboratory may also choose to use an oscillating or rotating saw so as not to break but rather cut the bones into small pieces. However, this technique requires that the operator be trained and thoroughly protected with respect to the high risks of injury during the handling of this instrument. The cutting additionally generates a very large amount of bone matter dust, which also requires the protection of the operator and the environment. The size of the bone fragments obtained is still very often too large and therefore requires a more precise second cut, which proves to be even more difficult, especially because of the fast speed of rotation or oscillation of the saw. This fast speed can also cause degradation of the DNA of the sample due to the induced heating. None of these solutions therefore makes it possible to work with precision on centimeter-scale samples.

Alternatively, a sampling method was developed based on cutting bone matrices using wood chisels. The friction of the wood chisel on the surface of the bone by rectilinear movements thus generates shavings. However, by harvesting the surface of the bone sample, this technique is limited to the area most exposed to external attacks and consequently that where the desired DNA has little chance of being usable. The implementation of this technique also requires a sufficient length of bone for proper intake as well as a certain know-how to collect bone matter and avoiding injury with the instrument. It also proves to be quite physical for the operator if a large number of bone fragments are to be treated and can generate musculoskeletal disorders (MSDs) when doing so. Lastly, the shavings generated are very delicate to handle using a tweezers to place them in a 1.5 or 2 mL microtube commonly used in molecular biology, due to static electricity.

Furthermore, in order to make the extraction and purification of the DNA more efficient, the protocols most commonly implemented use, at the end of the sampling, a grinder so as to reduce the collected bone fragment to powder.

In all cases, such grinding generally requires placing the bone fragment inside a steel bowl containing a bead, which requires complete decontamination between each sample. Once the bone matter is in the powder state, it is necessary to sample it between 60 and 100 mg in order to carry out the DNA extraction step. The weighing is carried out using a laboratory precision balance, the operation consisting of carefully and successively placing the bone powder in a 1.5 or 2 mL microtube placed on this scale by a spatula, so as to achieve the targeted mass of powder. The succession of steps of transferring and handling the sample is not highly recommended in this field given the high probability of contaminating the sample, losing material while the DNA is already present in a small amount, or even breaking the chain of traceability.

Therefore, it is clearly shown that the sampling methods used to date do not meet the criteria for standardization, simplicity, speed, high-throughput treatment, and safety.

Thus, a first aim of the present invention is to provide a device for taking samples of bone matter allowing an operator to be able to easily and accurately collect centimeter-scale bone fragments, without requiring excessive physical effort.

Another aim of the present invention is to provide a device for taking samples of bone matter that allows standardization, simplicity, speed and high-throughput treatment in a safe manner.

Another aim of the present invention is to provide a device for taking samples of bone matter that is transportable and allowing rapid and effective decontamination of the device between two sample collections.

Once the sampling step is finished, the operator is therefore usually in the presence of bone powder or shavings from which DNA is to be extracted. To this end, certain laboratories also use a chemical preparation based on phenol-chloroform and isoamyl alcohol preceded by a decalcification phase (EDTA, Proteinase K). The duration of such a method can easily exceed 24 hours, which makes it incompatible with fast and high-throughput processing, in particular in the context of identification of victims.

There are alternatively several machines dedicated to the extraction with their associated reagents. This is in particular the "Automate Express (ThermoFisher)" machine which uses magnetic silica bead technology or the "Qiacube (QIAGEN)" machine which uses silica column technology. Regardless of the machine selected, the cell lysis step lasts for about 2 hours 30 minutes and then the purification phase at least 1 hour with liquid transfer steps during the protocol that can lead to cross-contamination. In addition, these instruments can only treat about ten samples at a time, and their weights from 55 to 70 kg make it hard to consider transporting them outside the laboratory to extract DNA directly in the field.

Also, another purpose of the present invention is to provide an assembly making it possible to carry out the bone sampling step and the DNA extraction step in a standardized, simple, fast, high-throughput fashion.

Another purpose of the invention is to provide such an assembly for taking samples of standard samples to analyze the DNA directly at the sample collection site. "Standardization" means particular that an identical bone cylinder, called the bone core, can always be produced, regardless of the type of bone treated (long, flat, short, sesamoid, etc.).

These aims, as well as others which will appear subsequently, are achieved by a device for taking samples of bone matter intended to be mounted on a rotary tool such as a portable power tool, an orthopedic drill, or a dental motor, the device comprising:

- a support part positioned at the proximal end of the device, the support part being equipped with a means for coupling to a rotary tool, so as to rotationally drive the device;
- a trephine mounted removably on the support part, the trephine being equipped at its distal end with a cutting head intended to come into contact with the bone matter; the trephine and the support part being hollow and together defining an internal housing within the device; the cutting head comprising at its free end an opening to the outside of the device, the opening being in fluidic connection with the internal housing; and
- a removable collecting tube, positioned within the internal housing of the device and open at one of its ends substantially facing the opening of the cutting head, the collecting tube being intended to collect the bone matter cut by the trephine.

The presence of a removable collecting tube in the device for taking samples of bone matter according to the invention advantageously makes it possible to use this tube for multiple purposes during successive steps of sampling and analysis. This makes it possible to minimize the number of material transfers, and thus avoid possibly contaminating samples, as well as losing the traceability of the samples (by reducing the number of times they are handled). The device according to the invention thus offers mobility, standardization, simplicity, speed and high-throughput processing in a secure manner. Furthermore, the device for taking samples of bone matter is easily transportable and allows rapid and effective decontamination of the device between two sample collections.

Preferably, the collecting tube is made of a metallic material, typically stainless steel or titanium. The choice of titanium in particular for the collecting tube allows the tube to be reused over a very long operating period. The choice of titanium makes it possible to rapidly decontaminate the collecting tube between two samples without risk of oxidation.

Advantageously, the collecting tube is a consumable configured to be reusable after decontamination of the tube. This makes it possible to reuse the same collecting tube for numerous sampling, collection, and analysis operations, and thus allows a reduction in the costs of use. Alternatively, the collecting tube is a single-use consumable. In this case, it is not made of a metallic material, but a material having a lower production cost.

Preferably, the or each collecting tube comprises a unique marking or identifier; in particular, but not limited to, a barcode, a QR code, an identification tag or a unique identification number, typically an identification number affixed by etching on or in the collecting tube. This meets the need for traceability, which enters the field of the international standard ISO/IEC 17025, in particular necessary for COFRAC accreditation.

According to another aspect, the invention also relates to a kit for taking samples of bone matter comprising a device for taking samples of bone matter as described above, one or more collecting tubes(s) intended to be mounted within the sample-taking device and/or one or more additional trephine(s).

Preferably, the kit for taking samples of bone matter further comprises one or more tube closure cap(s), the or each closure cap being configured to hermetically close the open end of a collecting tube when the collecting tube is outside the device.

According to another aspect, the invention also relates to an assembly comprising a device for taking samples of bone matter as described above or a kit for taking samples of bone matter as described above; as well as a device for grinding the sampled bone matter, the device for grinding the bone matter being configured to receive the collecting tube of the sample-taking device and to grind the bone matter contained in said collecting tube. The use of such a device for grinding the bone matter makes it possible to transform the core produced by the sample-taking device, into bone powder. Such a bone powder makes it possible to obtain a larger reactive-matter contact surface, giving better genetic profiles during the genetic analysis operation, and thus making it possible to treat older and/or degraded bones. Such an assembly according to the invention is easily transportable because of its small bulk, and the portability of the tools that it proposes.

Preferably, the device for grinding the collected bone matter is a portable device, for example a grinding gun.

Advantageously, the assembly further comprises a bead arranged within the collecting tube containing the collected bone matter. This makes it possible to facilitate and make the grinding of the bone matter carried out by the grinding device more homogeneous. In particular, the addition of such a bead directly into the collecting tube coming from the sample-taking device, when it is combined with the presence of a closure cap on the collecting tube, makes it possible to obtain bone powder without having to transfer material between the sampling and grinding steps.

Preferably, the bone matter grinding device is provided with an adapter for tubes, said adapter consisting of a removable receptacle configured to receive at least one collecting tube, preferably configured to receive two collecting tubes. This makes it very easy to adapt the collecting tube from the sample-taking device to the grinding device. This compatibility offers a substantial advantage in that it makes it possible to avoid handling and transfers of contaminating material. Furthermore, the adapter is configured to allow effective retention of the metal collecting tubes in the grinding device, during the grinding operation.

According to another aspect, the invention also relates to a mobile laboratory formed from a transportable mobile container of the rolling cart type, for the collection, analysis and/or identification of biological materials, the mobile laboratory comprising a sample-taking device as described above or a sample-taking kit as described above or an assembly as described above, and being configured to define an isolated workspace for a human operator.

Preferably, the mobile laboratory further comprises a drill string comprising a rotary tool such as a portable power tool, an orthopedic drill, or a dental motor; and a vice intended to hold bone fragments while drilling. Such elements allow the bone fragments to be held while drilling.

Preferably, the mobile laboratory further comprises a means of genetic analysis of the automatic DNA extraction type.

According to another aspect, the invention also relates to a use of a sample-taking device as described above, wherein if the sample is taken with the device directly on a human being, said human being is not living. Such a use is for example particularly suitable for forensic scientists, in order to avoid large-scale, lengthy dissection for removal of the femur during autopsies It is specified that:

"standardized sampling", according to the present invention, means taking a sample of material with specific defined characteristics as a repeatable standard.

"bone matrix" means a biological sample which can be derived from all or part of the bone or dental tissue of a living being who was deceased at the time of collection, for example a human being.

"fast and high-throughput genetic analysis" means obtaining a genetic profile, most generally by STR (Short Tandem Repeat) genotyping. In the event of mass victim identification, the STR genotyping will preferentially be chosen and the protocol will have to make it possible to obtain a large number of genetic profiles in a few hours.

The description that follows, which is in no way limiting should be read with reference to the appended figures, among which:

FIG. 1 is a perspective view of an example of a device for taking samples of bone matter according to the present invention, the device comprising a removable collecting tube;

FIG. 2 is a side view of the sampling device of FIG. 1;

FIG. 3 is a longitudinal cross sectional view taken along the cutting plane III-III of the sample-taking device of FIG. 2;

FIG. 4 is a perspective view of an embodiment of a tube adapter, such an adapter being configured to receive the collecting tube from FIG. 1 and being intended to equip a bone matter grinding device; and FIG. 5 is a perspective view of a mobile laboratory example according to the invention, in the form of a transportable mobile container, the mobile laboratory comprising the device for taking samples of bone matter of FIG. 1.

FIGS. 1 to 3 show a device 1 for taking samples of bone matter according to the invention. The device 1 is intended to be mounted on a rotary tool (not shown) such as a portable power tool, an orthopedic drill, or a dental motor, allowing the rotation of the device 1. The device 1 extends longitudinally along an axis A1 (which is also its axis of rotation), and has a proximal end 3, intended to be connected to the rotary tool, and a distal end 5 intended to cut bone matter. The device 1 advantageously forms part of an assembly (not shown) comprising, in addition to the sample-taking device 1, a device for grinding the collected bone matter (such a grinding device not being shown in the figures). Without this being limiting, the grinding device is typically a portable device of the grinding gun type. The grinding gun is typically "T" shaped. This grinding gun can be, for example, a portable grinding gun such as the Super FastPrep-2 instrument of the brand MP BIOMEDICALS®. Alternatively or additionally, the device 1 can also be part of a mobile laboratory 40, as will be described below.

The sampling device 1 comprises a support part 2 and a trephine 4 removably mounted on the support part 2. The trephine 4 and the support part 2 are hollow and together define an internal housing 6 within the device 1. The sampling device 1 further comprises a removable collecting tube 8, positioned within the internal housing 6. The collecting tube 8 is intended to collect the bone matter cut by the trephine 4.

The support part 2 is arranged at the proximal end 3 of the device 1 and forms a rotating part that is connected to the rotary tool. To do this, a mandrel (for example of the "quick connect" type) can connect the support part 2 to the rotary tool. Any type of mandrel can be used, for example a mandrel of the universal and automatic drill mandrel type. The support part 2 forms a generally tapered and tubular part, and comprises means 10 for coupling to the rotary tool, in particular to the mandrel for connecting thereto. The coupling means 10 are for example made up of a proximal portion 12 of the part 2, finer in diameter than a distal portion 14 of the latter, and intended to be inserted into and held by clamping within the mandrel. The support part 2 is for example made of stainless steel.

The trephine 4 is for example mounted on the support part 2 by means of a clamping tool of the clamp type. The trephine 4 is provided at its distal end 5 with a cutting head 16 intended to come into contact with the bone matter. The cutting head 16 comprises at its free end an opening 18 that opens outside the device 1. The opening 18 is at the end of an internal channel 20 that extends longitudinally inside the trephine 4, along the axis A1. The internal channel 20 is in fluidic connection with the internal housing 6. The cutting head 16 comprises a ring that penetrates into the bone matter and cuts the fragments, which are evacuated into the internal channel 20 via the opening 18.

In the particular embodiment shown in FIGS. 1 to 3, the trephine 4 comprises, in addition to the cutting head 16, an adapter part 22 intended to be mounted (in particular by screwing) on the support part 2, as well as a nut 24 connecting the adapter part 22 to the cutting head 16. The adapter part 22 and the nut 24 are hollow and together define the internal channel 20. The adapter part 22 has a substantially frustoconical shape, which defines a rotational symmetry. The nut 24, which is for example a mandrel nut, is typically attached to the adapter part 22 by means of an elastically deformable inner hollow clamp 26. The inner hollow clamp 26 is integral with the nut 24 and inserted into an opening 27 opening from a sleeve 28 extending at one end of the adapter part 22. The elastic effect of the arms of the clamp 26 thus makes it possible to retain the nut 24 on the part 22 and to prevent any longitudinal movement thereof during the use of the device 1. The outer wall of the nut 24 then extends around the sleeve 28. The cutting head 16 is inserted into the mandrel nut 24 and held by clamping therein. Via this arrangement between the support part 2 and the trephine 4, the trephine 4 is thus configured to be rotated by the support part 2 when that part is connected to the rotary tool, the rotation being carried out around the axis of rotation A1. The trephine 4 is for example made of stainless steel.

Typically, the adapter part 22 is for example made of SAE 316L grade stainless steel, while the cutting head 16 can be made of X30Cr13 type stainless steel. The desired qualities are the longevity of the sharpness in order to reduce heating and non-alteration by oxidation following decontamination.

The collecting tube 8 is closed at one of its ends 29A, and open at its other end 29B. The open end 29B of the tube 8 is arranged substantially opposite the internal channel 20, and therefore the opening 18 of the cutting head 16. The collecting tube 8, arranged in the internal housing 6, is partially housed in a recess 31 provided inside the support part 2. A support washer 25 can be inserted around the open end 29B of the tube 8, between the tube 8 and an inner bushing 33 protruding from the inner wall of the part 22, to facilitate the assembly of the whole. The collecting tube 8 is preferably made of a metallic material, typically stainless steel or titanium. According to one particular embodiment of the invention, the collecting tube 8 is a consumable configured to be reusable after decontamination of the tube. According to another particular embodiment, the collecting tube 8 can contain a bead (not shown in the figures), for example a metal bead, and in particular made of stainless steel.

The collecting tube 8 comprises preferably a unique marking or identifier; in particular, but not limited to, a barcode, a QR code, an identification tag or a unique identification number, typically an identification number affixed by etching on or in the collecting tube 8.

The sample-taking device 1 is intended to be light, robust, of secure use for its operator and easily decontaminated in particular by sterilization in order to avoid any risk of contamination between the samples. The sampling device 1 makes it possible to cut the bone matter in the form of a core that will be collected in the collecting tube 8. The bone cores obtained are then all of a standardized length and diameter. They can thus be easily handled, transported or stored in collecting tubes 8. The coring is preferentially carried out at a low speed of rotation depending on the characteristics of the rotary tool chosen.

Once removed from the sampling device 1 (by manual detachment of the trephine 4 from the support part 2), the collecting tube 8 containing the collected bone matter can be closed by a cap 30 for closing the tube (visible in FIG. 4). The closure cap 30 is configured to hermetically close the open end 29B of the collecting tube 8. The collecting tube 8 can then be placed, for example, in the device for grinding bone matter. To do this, the grinding device may be provided with an adapter 32 for tubes, such an adapter 32 being shown in FIG. 4. The adapter 32 consists of a removable receptacle configured to receive the collecting tube 8. Preferably, and as shown in FIG. 4, the receptacle 32 is configured to receive two distinct collecting tubes 8. The receptacle 32 is preferentially closed by a cover 34 and is intended to be attached within the grinding device, for example by screwing. The cover 34 is slid into a groove 36 provided on the receptacle, then is retained and tightened by means of a screw (not shown) which is attached between the two tube closure caps 30.

FIG. 5 shows a mobile laboratory 40 for collecting, analyzing and/or identifying biological materials, comprising the sampling device 1 according to the invention. The mobile laboratory 40 may also comprise the portable grinding device, provided with its adapter 32.

The mobile laboratory 40 is formed of a transportable mobile container of the rolling cart type, and is configured so as to define an isolated workspace for a human operator. To do this, the rolling cart 40 comprises, for example, a case 42 mounted on four rolling feet (not shown in the figures), provided with storage spaces 46 and topped by a cover 48. An extension table (not shown), mounted on rolling feet, can also be provided in the rolling cart 40.

In addition to the sampling device 1 and the grinding device, the mobile laboratory 40 can also comprise a means for the genetic analysis of the collected bone matter from the grinding device. This genetic analysis means (not shown in the figures for reasons of clarity) may be, for example, a portable automaton enabling the extraction of DNA such as the instrument PDQex 2400 of the Zygem® brand making it possible to treat 24 samples in 20 minutes. The reagents used for the extraction phase are also optimized to treat bone matrices.

The mobile laboratory 40 may also comprise a drill string comprising a rotary tool of the portable power tool, an orthopedic drill, or even a dental motor; as well as a vice for holding bone fragments during drilling. The drill string, portable power tool and vice are not shown in FIG. 5. Such elements allow the bone fragments to be held while drilling.

One of the uses of the present solution is mass victim identification following, for example, an air disaster resulting in hundreds or thousands of fragmented human remnants, in a highly degraded state. According to the DNA analysis protocol conventionally used for the purposes of identification of the victims (which may typically be an ICMP protocol, for the International Commission on Missing Persons), it is necessary to send each of these bone fragments to the analysis laboratory under refrigerated conditions, then sample and analyze each of these fragments. With current solutions, this operation requires heavy, complex logistics given the storage volume that this kind of disaster requires.

On the contrary, the implementation of the present invention makes it possible, in such a case, to drill bone matrices on each of the bone fragments as close as possible to the site of the disaster. Preliminary studies carried out on different types of human bone tend to demonstrate that the amount of material necessary to obtain a DNA profile corresponds to 3 or 5 bone cores. The cores derived from each sampled bone fragment can thus be gathered in a collecting tube, for example of 2 mL, having a unique barcode identifier. At the end of the sampling phase, the samples can either be directly analyzed on site within a mobile DNA laboratory, or conveyed to a conventional laboratory. The logistics are then greatly simplified, depending on the implementation of this solution, 96 samples can thus be stored in a cryobox (for example a cryobox with the dimensions of (L×W×H) 25×12×5 cm).

Another use of the present solution would be to identify the gathered bone fragment DNA in blocks. Here again, the simplicity, speed and standardization of the sampling method make it possible to directly carry out the sampling and analysis on-site, or failing that, to convey only the samples to the laboratory while storing the bones on the human remains site.

The present invention has been described with reference to a device 1 for taking samples of bone matter comprising a single trephine 4 and a single collecting tube 8. The invention also relates to a kit for taking samples of bone matter comprising, in addition to the sample-taking device 1, one or more collecting tubes 8 and/or one or more additional trephine(s) 4 (of different sizes and/or diameters). The kit may also include one or more tube 8 closure cap(s) 30.

The invention claimed is:

1. A device for taking samples of bone matter intended to be mounted on a rotary tool including a portable power tool, an orthopedic drill, or a dental motor, the device comprising:

a support part positioned at the proximal end of the device, the support part being equipped with a means for coupling to the rotary tool, so as to rotationally drive the device about an axis of rotation;

a hollow cylindrical trephine mounted removably and coaxially on the support part, the trephine defining a longitudinal internal channel extending axially and longitudinally inside the trephine along said axis of rotation, the trephine being equipped at its distal end with a cutting head intended to come into contact with the bone matter, the cutting head forming a coring edge, the cutting head comprising at a free end thereof an axial opening being at an end of the longitudinal internal channel and constituting an entrance of said longitudinal internal channel that opens to the outside of the device, the trephine and the support part being hollow and together defining an internal housing within the device and aligned coaxially with the longitudinal internal channel, the cutting head comprising at its free end an opening which opens to the outside of the device, the opening being in fluidic connection with the internal housing; and a removable collecting tube, positioned within the internal housing of the device and open at one of its ends substantially facing the longitudinal internal channel and the opening of the cutting head, the collecting tube being intended to collect the bone matter cut by the trephine, the collecting tube being hollow and arranged in direct axial continuity with the longitudinal internal channel so that the bone matter entering through the axial opening of the cutting head is conveyed directly into the collecting tube without passing through an intermediate collection chamber;

wherein the collecting tube is removable from the device as a closed sampling container.

2. The sample-taking device according to claim 1, characterized in that the collecting tube is made of a metallic material including stainless steel or titanium.

3. The sample-taking device according to claim 1, characterized in that the collecting tube is a consumable configured to be reusable after decontamination of the tube.

4. A collection kit for taking samples of bone matter comprising a device for taking samples of bone matter, one or more collecting tubes intended to be mounted within the sample-taking device and/or one or more additional hollow cylindrical trephines, characterized in that the device for taking samples of bone matter is in accordance with claim 1.

5. The collection kit according to claim 4, characterized in that it further comprises one or more closure caps closing a respective open end of the one or more collecting tubes, respectively, or each closure cap being configured to hermetically close a respective open end of a respective collecting tube of the one or more collecting tubes when the respective collecting tube is outside the device.

6. An assembly comprising the device for taking samples of bone matter according to claim 1 or a kit for taking samples of bone matter comprising the device for taking samples of bone matter according to claim 1; and a device for grinding the sampled bone matter, the device for grinding the sampled bone matter being configured to receive the collecting tube of the sample-taking device and to grind the bone matter contained in said collecting tube without prior removal of the bone matter from the collecting tube.

7. The assembly according to claim 6, characterized in that the device for grinding the collected bone matter is a portable device.

8. The assembly according to claim 6, characterized in that it further comprises a bead positioned inside the collecting tube together with the bone matter.

9. The assembly according to claim 6, characterized in that the bone matter grinding device is provided with an adapter for tubes, said adapter consisting of a removable receptacle configured to receive at least one collecting tube.

10. A mobile laboratory formed from a transportable container for the collection and/or analysis of biological material, the mobile laboratory comprising:

the sample-taking device of claim 1; or a collection kit for taking samples of bone matter comprising:

the sample-taking device of claim 1;

the collecting tube intended to be mounted within the sample-taking device of claim 1; and one or more additional hollow cylindrical trephines; or an assembly comprising:

the sample-taking device of claim 1; and a device for grinding the sampled bone matter, the device for grinding the sampled bone matter being configured to receive the collecting tube of the sample-taking device of claim 1 and to grind the bone matter contained in said collecting tube without prior removal of the bone matter from the collecting tube, wherein the mobile laboratory further comprises:

an isolated workspace configured to limit external contamination; and a genetic analysis module comprising an automatic DNA extraction device configured to process the bone matter collected by the sample-taking device.

11. The mobile laboratory according to claim 10, characterized in that it further comprises a drill string comprising the rotary tool including the portable power tool, the orthopedic drill, or the dental motor; and a vice for holding bone fragments during drilling.

12. The mobile laboratory according to claim 10, wherein the isolated workspace comprises contamination control means including environmental control means configured to regulate airflow and temperature within the workspace.

13. A use of a device according to claim 1 for the collection of bone matter, characterized in that if the sample is taken with the device directly on a human being, said human being is not living.

* * * * *